(12) United States Patent
Mei-Dan et al.

(10) Patent No.: US 12,310,619 B2
(45) Date of Patent: May 27, 2025

(54) SLOTTED CANULLA FOR ARTHROSCOPIC SURGERY

(71) Applicant: Smith & Nephew, Inc., Memphis, TN (US)

(72) Inventors: Omer Mei-Dan, Boulder, CO (US); Jacob Segil, Boulder, CO (US)

(73) Assignee: SMITH & NEPHEW, INC., Memphis, TN (US)

( * ) Notice: Subject to any disclaimer, the term of this patent is extended or adjusted under 35 U.S.C. 154(b) by 227 days.

(21) Appl. No.: 16/766,248

(22) PCT Filed: Dec. 3, 2018

(86) PCT No.: PCT/US2018/063680
§ 371 (c)(1),
(2) Date: May 21, 2020

(87) PCT Pub. No.: WO2019/109100
PCT Pub. Date: Jun. 6, 2019

(65) Prior Publication Data
US 2021/0038255 A1 Feb. 11, 2021

Related U.S. Application Data

(60) Provisional application No. 62/593,663, filed on Dec. 1, 2017.

(51) Int. Cl.
*A61B 17/34* (2006.01)
*A61B 17/00* (2006.01)
*A61B 17/32* (2006.01)

(52) U.S. Cl.
CPC .... *A61B 17/3421* (2013.01); *A61B 17/00234* (2013.01); *A61B 17/320016* (2013.01);
(Continued)

(58) Field of Classification Search
CPC .......... A61B 17/3421; A61B 17/00234; A61B 17/320016; A61B 17/3417;
(Continued)

(56) References Cited

U.S. PATENT DOCUMENTS

| 4,022,191 A | 5/1977 | Jamshidi |
| 4,337,761 A * | 7/1982 | Upsher .................... A61B 1/07 600/196 |

(Continued)

FOREIGN PATENT DOCUMENTS

| WO | 2012134912 | 10/2012 |
| WO | 2012145048 | 10/2012 |

(Continued)

OTHER PUBLICATIONS

International Search Report and Written Opinion dated Feb. 11, 2019 in Application No. PCT/US2018/063680.
(Continued)

*Primary Examiner* — Anh T Dang
(74) *Attorney, Agent, or Firm* — ArentFox Schiff LLP; Joseph M. Maraia; Marlo Schepper Grolnic

(57) ABSTRACT

A slotted cannula for surgical procedures is disclosed. The slotted cannula has an elongated semi-circular body comprising a cavity extending along a longitudinal axis of the semi-circular body, the cavity having an open distal end and an open proximate end and an integrally formed outward bend extending curvilinear from the cavity on the proximate end and at least one fold line across the width of the cannula, perpendicular to the longitudinal axis. The cannula can be bent or broken along the at least one fold line to adjust the operable length of the cannula during a surgical procedure.

4 Claims, 3 Drawing Sheets

(52) U.S. Cl.
CPC ............... *A61B 2017/00309* (2013.01); *A61B 2017/00871* (2013.01); *A61B 2017/3443* (2013.01)

(58) Field of Classification Search
CPC .. A61B 2017/00309; A61B 2017/3443; A61B 2017/00946; A61B 2017/00871
See application file for complete search history.

(56) References Cited

U.S. PATENT DOCUMENTS

| | | | |
|---|---|---|---|
| 5,234,445 A | 8/1993 | Walker et al. | |
| 5,779,697 A | 7/1998 | Glowa et al. | |
| 9,011,323 B2 * | 4/2015 | Vayser | A61B 1/07 600/203 |
| 2007/0049946 A1 | 3/2007 | Mackley et al. | |
| 2007/0270898 A1 | 11/2007 | Lillehei | |
| 2007/0276288 A1 | 11/2007 | Khaw | |
| 2009/0131907 A1 | 5/2009 | Chin et al. | |
| 2009/0222044 A1 * | 9/2009 | Gorek | A61B 17/0218 606/279 |
| 2010/0191178 A1 | 7/2010 | Ross et al. | |
| 2010/0280316 A1 | 11/2010 | Dietz et al. | |
| 2011/0054484 A1 | 3/2011 | Brandon | |
| 2011/0144447 A1 | 6/2011 | Schleitweiler et al. | |
| 2012/0123389 A1 | 5/2012 | Shafran | |
| 2014/0088354 A1 | 3/2014 | Mirza et al. | |
| 2015/0133733 A1 | 5/2015 | Weiman et al. | |
| 2016/0346513 A1 | 12/2016 | Swaney et al. | |

FOREIGN PATENT DOCUMENTS

| | | |
|---|---|---|
| WO | 2012157878 | 11/2012 |
| WO | 2018083619 | 5/2018 |

OTHER PUBLICATIONS

European Search Report dated Jun. 17, 2021 in European Application No. 18884169.6.

* cited by examiner

210

220

201
100

SLOTTED CANULLA FOR ARTHROSCOPIC SURGERY

CROSS REFERENCE TO RELATED APPLICATIONS

This application is a U.S. national stage entry under 35 U.S.C. § 371 of International Application No. PCT/US2018/063680 filed Dec. 3, 2018 entitled "SLOTTED CANULLA FOR ARTHROSCOPIC SURGERY," which claims priority to, and the benefit of, U.S. Provisional Patent Application Ser. No. 62/593,663, filed on Dec. 1, 2017, the entire contents of which are incorporated herein by reference in their entirety.

TECHNICAL FIELD

This invention relates generally to the field of medical devices and, in particular, to a slotted cannula for arthroscopic operations.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Compared to open surgery, endoscopic surgery may result in shorter hospital stays, or allow outpatient treatment.

Among more recent developments and advances in endoscopic surgical procedures, arthroscopic surgery employing the use of endoscopic devices has found widespread application. Arthroscopic surgical procedures enable closed surgery to be performed via portals through which a variety of elongated instruments may be passed to gain access to an internal surgical work site. Very often a cannula is inserted into the portal in order to provide a convenient passageway through which various instruments may pass. The variety of instruments which must be inserted through the cannula includes instruments of varying sizes and configurations. While the instrument shafts are usually cylindrical, some instruments may have unusually large or sharp distal tips which may cut the cannula upon the insertion or extraction of the instrument, thus making it less suitable for subsequent instruments which must be inserted during the same surgical procedure. It is desirable, therefore, to devise a cannula which minimizes these problems.

SUMMARY

This disclosure provides a slotted cannula with improved design and reduced cost. One aspect of the present invention relates to a cannula for a surgical procedure. The cannula comprises an elongated semi-circular body comprising a cavity extending along a longitudinal axis of the semi-circular body, the cavity having an open distal end and an open proximate end. The cannula includes an integrally formed outward bend extending curvilinear from the cavity on the proximate end. The cannula also includes at least one fold line across the width of the cannula, perpendicular to the longitudinal axis. The cannula is preferably made from a polymer material, and can be bent or broken along the at least one fold line to adjust the operable length of the cannula during a surgical procedure.

The outward bend of these cannulas may angle away from the longitudinal axis of the cavity at an angle between 30 and 50 degrees. For example, the outward bend may angle away from the longitudinal axis of the cavity at an angle of about 45 degrees.

These cannulas may further comprise a slot extending longitudinally from the proximal end towards the distal end.

These cannulas may be made from a polymeric material selected from the group consisting of polyacrylate, polycarbonate, polystyrene, glycol modified polyethylene terephthalate, and cellulose acetate butyrate.

These cannulas may have an inner diameter in a range of 1-20 mm, for example, an inner in a range of 10-18 mm, for example, an inner diameter of about 15 mm.

These cannulas may have an outer diameter in a range of 10-40 mm.

These cannulas may have a longitudinal length in a range of 100-400 mm.

These cannulas may have between 2 and 5 fold lines separated along the longitudinal length of the cannula, for example, separated along the longitudinal length of the cannula at a distance in the range of 5-20 mm.

Another aspect of the present invention relates to an instrument kit for implementing an surgical procedure. The kit includes a cannula comprising an elongated semi-circular body comprising a cavity extending along a longitudinal axis of the semi-circular body, the cavity having an open distal end and an open proximate end, an integrally formed outward bend extending curvilinear from the cavity on the proximate end, and at least one fold line across the width of the cannula, perpendicular to the longitudinal axis, wherein the cannula is made from a polymer material, and wherein the cannula can be bent or broken along the at least one fold line to adjust the operable length of the cannula during a surgical procedure; and, a plunger that may be attached to the cannula to aid in insertion of the cannula into a surgical cavity. These instrument kits may also include an endoscope sized for insertion along said cannula for direct visualization of an operative site.

A method for implementing a surgical procedure. The procedure includes making an incision on a patient in need of such surgical procedure at a location proximate an operation site to establish an entry portal; attaching a plunger to a longitudinal bore of a cannula for surgical procedures, said cannula comprising: an elongated semi-circular body comprising:

a cavity extending along a longitudinal axis of the semi-circular body, the cavity having an open distal end and an open proximate end; an integrally formed outward bend extending curvilinear from the cavity on the proximate end; and, at least one fold line across the width of the cannula, perpendicular to the longitudinal axis, wherein the cannula is made from a polymer material, and wherein the cannula can be bent or broken along the at least one fold line to adjust the operable length of the cannula during a surgical procedure. The distal end of the cannula/plunger combination is inserted into the entry portal and advanced to a predetermined distance relative to the operation site. The plunger is then withdrawn while permitting the cannula to remain in place at the operation site. An endoscope is then inserted along the cavity of the cannula for direct visualization of anatomic structures surrounding the cannula and positioning of the cannula at the operative site. The endoscope is withdrawn from the cannula, and a surgical instrument comprising a cutting instrument is inserted along the cannula and advanced so that the cutting instrument is in contact with a target tissue at the operation site. The target tissue is operatively engaged with the surgical instrument so as to perform a desired operative procedure on the target tissue. The surgical instrument is withdrawn from the cannula, and the cannula is withdrawn through the entry portal.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

DETAILED DESCRIPTION

The following detailed description of example implementations refers to the accompanying drawings. The same reference numbers in different drawings may identify the same or similar elements.

Figure 1:
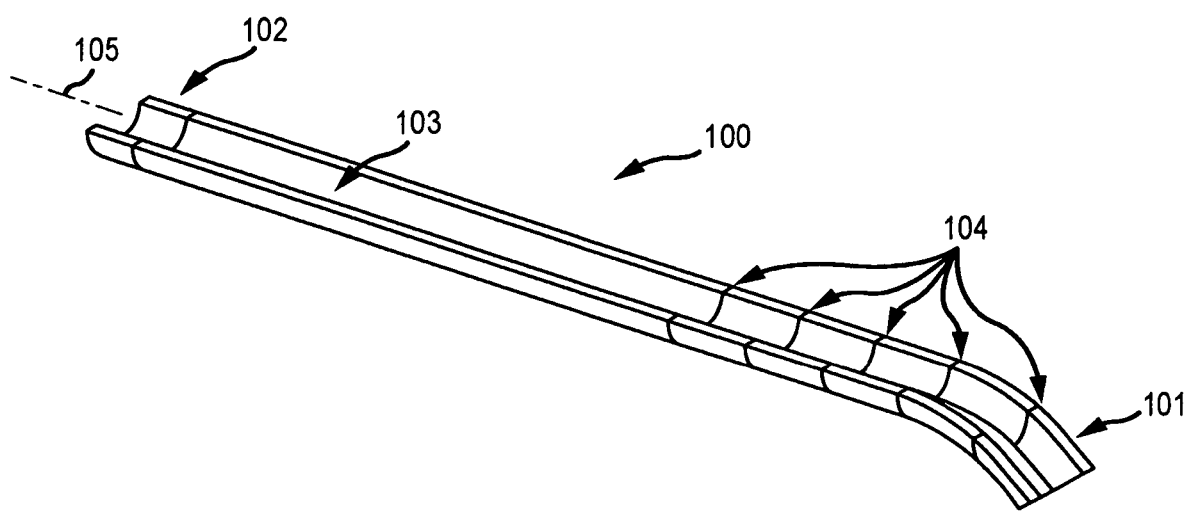
FIG. 1 is a perspective view of a cannula of the present disclosure.

FIG. 1 is a perspective view of a slotted cannula 100 described herein. As shown in FIG. 1, slotted cannula 100 may include a proximal end 101, a distal end 102, and a cavity 103. Slotted cannula 100 may include one or more fold lines or "vertebrae" 104 that comprise a score in the material of the cannula 100 and that can be easily bent or broken to easily adjust the size of the cannula during use in arthroscopic surgical procedures. Proximal end 101 may be bent out of the longitudinal axis 105 of cavity 103. The bend may be away from the longitudinal axis 105 of cavity 103 at an angle between 30 and 50 degrees; or an angle of about 45 degrees.

Figure 2A:
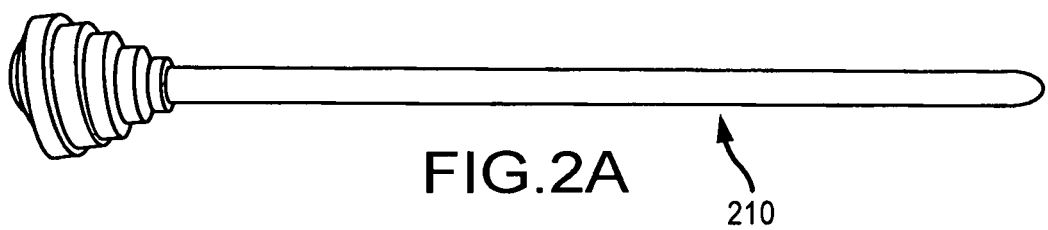
FIG. 2A shows a plunger useful for insertion of the cannula of FIG. 1.
Figure 2B:
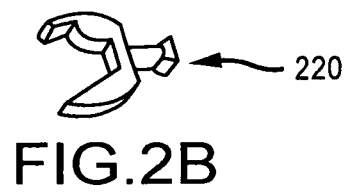
FIG. 2B shows a clip that can be used to attach the cannula of FIG. 1 to the plunger of FIG. 2.
Figure 2C:
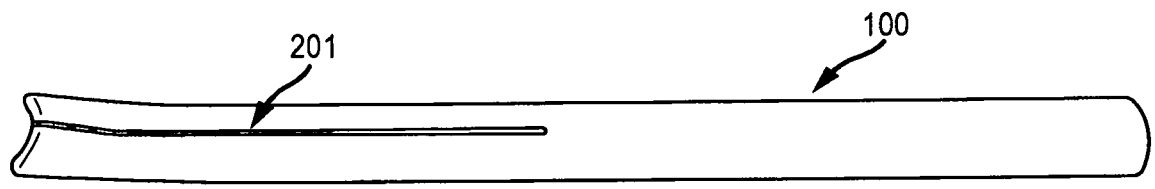
FIG. 2C shows a view of the back side of a cannula of the present disclosure.

Referring to FIG. 2C, which is a view of the back of the cannula, the cannula 100 includes a slot 201 that extends longitudinally from the proximal end 101 towards the distal end 102. This slot allows greater flexibility and expandability of the cannula of this disclosure compared with metal or other cannulas that do not include a corresponding slot.

Cavity 103 may be configured to permit various components to be inserted into, extruded from, and/or removed from slotted cannula 100. For example, cavity 103 may permit an endoscope, a guidewire, an anchor assembly, an anchor driver, a graft construct, a graft pusher, a suture tool, and/or the like, to be inserted into slotted cannula 100 and access an arthroscopic cavity through slotted cannula 100.

Slotted cannula 100 may be comprised of any suitable material to permit access to a spinal segment through an incision. For example, slotted cannula 100 may be comprised of a composite polymeric, a thermoplastic, an alloy, and/or the like. Preferably, slotted cannula 100 is comprised of a plastic material such that cannula 100 is inexpensive and disposable. Suitable plastic materials that may compose the cannula of this disclosure are selected from the group consisting of polyacrylate, polycarbonate, polystyrene, glycol modified polyethylene terephthalate, and cellulose acetate butyrate.

FIG. 2A shows a plunger 210 that can be used to aid in the insertion of cannula 100. FIG. 2B shows a clip that may be used to attach cannula 100 to plunger 210, for example, during insertion of cannula 100 into an arthroscopic cavity.

Figure 3A:
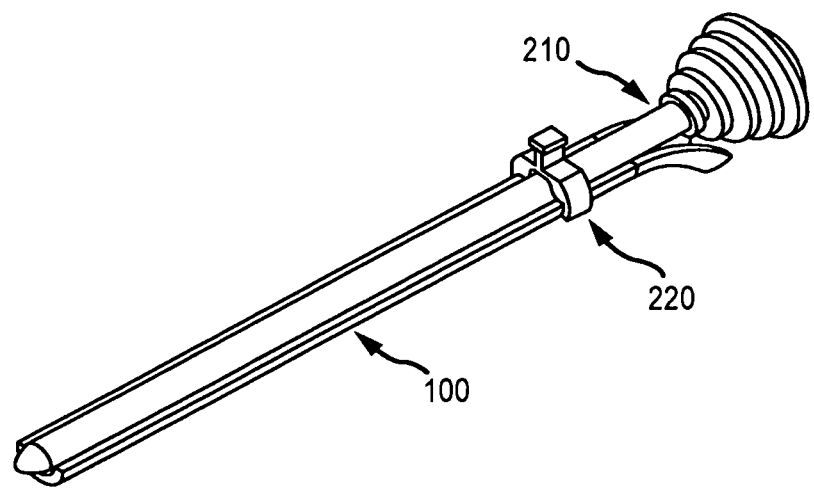
FIG. 3A is a front perspective view of the cannula of FIG. 1 attached to the plunger of FIG. 2A by clip FIG. 2B.
Figure 3B:
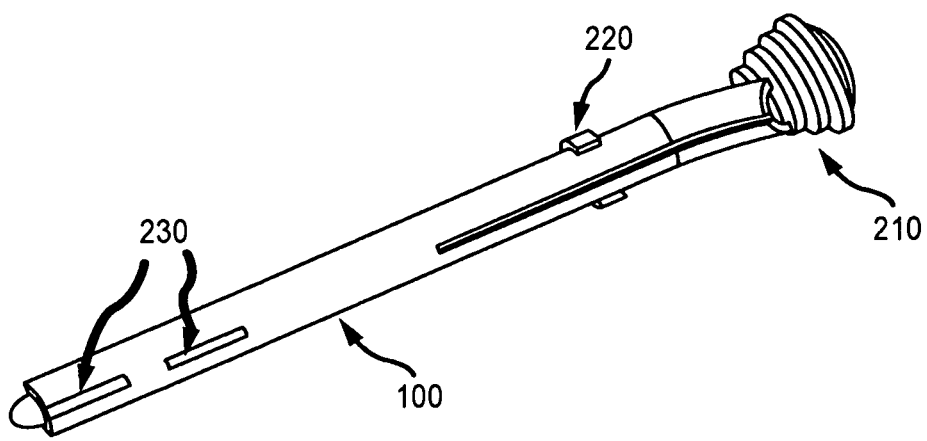
FIG. 3B is a back perspective view of the cannula of FIG. 1 attached to the plunger of FIG. 2A by clip FIG. 2B.

FIGS. 3A and 3B depict cannula 100 attached to plunger 210 by clip 220, for example prepared for insertion into an arthroscopic cavity. FIG. 3B depicts optional tunnel 230 on the back of the cannula 100. A stitch may be shuttled through the tunnel 230 prior to insertion of the cannula 100, via a small guide loop.

As an example, slotted cannula 100 may include an elongated, substantially semi-circular shape, and include an outer diameter between about 8 millimeters (mm) and 40 mm or preferably about 20 mm; and an inner diameter of between about 5 mm and 35 mm or preferably about 15 mm. Additionally, as an example, cannula 100 may have a longitudinal length of between about 50 millimeters (mm) and 400 mm or preferably about 210 mm. It should be understood that implementations described herein are applicable to many other types of configurations than shown in FIG. 1.

In embodiments, the cannula 100 has an inner diameter in the range of 1-20 mm, preferably 10-18 mm, and more preferably about 15 mm.

In embodiments, the cannula 100 has an outer diameter in the range of 10-40 mm, preferably 15-30 mm, and more preferably about 20 mm.

In embodiments, the cannula 100 has a length in the range of 100-400 mm, preferably 180-240 mm, and more preferably about 210 mm.

In embodiments, the cannula 100 comprises at least one fold line 104 that comprises a score running crosswise across the width of the cannula 100 perpendicular to the longitudinal axis 105 of the cannula 100. The cannula 100 may have 1, 2, 3, 4, or 5, or more fold lines 105. The fold lines 104 may be separated along the length of the cannula at a distance in the range of 5-20 mm, preferably 8-15 mm, and more preferably about 10 mm. Preferably, the fold lines 104 are grouped proximate the proximate end 101 of cannula 100. The fold lines 104 allow the intervening sections of the cannula 100 to be bent back or broken off the cannula 100 to adjust the size of the cannula during use.

Another aspect of the present invention relates to an instrument kit for implementing an arthroscopic surgical procedure. The instrument kit comprises a cannula 100 of this disclosure, and a plunger that may be attached (e.g., by being clipped to the cannula) to the cannula to aid in insertion of the cannula into an arthroscopic cavity. The endoscopic surgical procedure may be a procedure selected from the group consisting of carpal tunnel release, cubital tunnel release, plantar fascia release, lateral release for patella realignment, release of radial tunnel, release of pronatar teres, release of trigger finger, release of lacertous fibrosis, release of the extensor tendons for lateral epicondylitis, release of medial epicondylitis, release of the posterior and other compartments of the leg, forearm fascia release for fascial compartment syndrome, and release of fascial compartments in the upper and lower extremity. The instrument kit may further comprise an endoscope sized for insertion along the cannula for direct visualization of an operative site. The endoscope may be capable of carrying a cutting instrument at a leading end. Thus, the instrument kit may further comprise a cutting instrument mountable to the leading end of the endoscope. In another embodiment, the instrument kit may further include a second endoscope with a cutting instrument mounted at a leading end of the second endoscope. The second endoscope is insertable along the cannula.

Another aspect of the present invention relates to a method for implementing a uniportal arthroscopic surgical procedure using the slotted cannula of the present invention. In these methods, the endoscopic surgical procedure may be a procedure selected from the group consisting of carpal tunnel release, cubital tunnel release, plantar fascia release, lateral release for patella realignment, release of radial tunnel, release of pronatar teres, release of trigger finger, release of lacertous fibrosis, release of the extensor tendons for lateral epicondylitis, release of medial epicondylitis, release of the posterior and other compartments of the leg, forearm fascia release for fascial compartment syndrome, and release of fascial compartments in the upper and lower extremity.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:
1. A method for implementing a surgical procedure, comprising:
a) making an incision on a patient in need of such surgical procedure at a location proximate an operation site to establish an entry portal;
b) attaching a plunger to a longitudinal bore of a cannula for surgical procedures, said cannula comprising:
an elongated semi-circular body comprising:
a cavity extending along a longitudinal axis of the semi-circular body, the cavity having an open distal end and an open proximate end;
an integrally formed outward bend extending curvilinear from the cavity on the proximate end; and,
at least one fold line across a width of the cannula, perpendicular to the longitudinal axis,
wherein the cannula is made from a polymer material, and
wherein the cannula can be bent or broken along the at least one fold line to adjust the operable length of the cannula during a surgical procedure
c) introducing the distal end of the cannula/plunger combination into the entry portal and advancing the combination a predetermined distance relative to the operation site;
d) withdrawing the plunger while permitting the cannula to remain in place at the operation site;
e) inserting an endoscope along the cavity of the cannula for direct visualization of anatomic structures surrounding the cannula and positioning of the cannula at the operative site;
f) withdrawing the endoscope from the cannula;
g) inserting a surgical instrument comprising a cutting instrument into the cannula;
h) advancing the surgical instrument so that the cutting instrument is in contact with a target tissue at the operation site;
i) operatively engaging the target tissue with the surgical instrument so as to perform a desired operative procedure on the target tissue;
j) withdrawing the surgical instrument from the cannula; and
k) withdrawing the cannula through the entry portal.
2. The method of claim 1, wherein the at least one fold line extends across an entire width of the cannula.
3. A cannula for a surgical procedure, comprising:
an elongated semi-circular body comprising:
a proximal end, a distal end, and a longitudinal axis extending between the proximal and distal ends, the body including an integrally formed outward bend extending at an angle from the longitudinal axis at the proximal end of the body;
a cavity extending along the longitudinal axis of the body, the cavity having an open end at a distal terminus of the body, and an open end at a proximal terminus of the integrally formed outward bend, a width of the cavity being fixed along an entire length of the body between the distal terminus of the body and the proximal terminus of the integrally formed outward bend;
a slot defined by the body extending from the open end at the proximal terminus of the outwardly extending bend to the open end of the distal terminus of the body, the slot in communication with the cavity and with the open end of the distal terminus of the body, a width of the slot being constant between the proximal terminus of the integrally formed outward bend and the distal terminus of the body; and
at least one tunnel extending from the distal terminus of the body along the longitudinal axis, the at least one tunnel configured for passage of a guide loop.

4. The cannula of claim 3, further comprising a clip attachable to the body.

\* \* \* \* \*